US00RE33976E

United States Patent [19]

Nishikawa et al.

[11] E Patent Number: Re. 33,976

[45] Reissued Date of Patent: Jun. 30, 1992

[54] GRANULAR FERTILIZER COMPOSITIONS

[75] Inventors: Akira Nishikawa, Hyogo; Hiromichi Oshio, Osaka, both of Japan

[73] Assignee: Sumitomo Chemical Co., Ltd., Osaka, Japan

[21] Appl. No.: 662,307

[22] Filed: Feb. 28, 1991

Related U.S. Patent Documents

Reissue of:

[64] Patent No.: 4,913,725
Issued: Apr. 3, 1990
Appl. No.: 50,453
Filed: May 18, 1987

[30] Foreign Application Priority Data

May 16, 1986 [JP] Japan ..... 61-113402
Jun. 11, 1986 [JP] Japan ..... 61-135591

[51] Int. Cl.[5] ..... A01N 43/653

[52] U.S. Cl. ..... 71/92; 71/122; 71/11; 71/DIG. 1

[58] Field of Search ..... 71/1, 11, 65, 92, 122, 71/DIG. 1

[56] References Cited

U.S. PATENT DOCUMENTS 4,138,344 2/1979 Choi et al. ..... 71/64.11 X
4,469,502 9/1984 Heller et al. ..... 71/64.07
4,913,725 4/1990 Nishikawa et al. ..... 71/92

FOREIGN PATENT DOCUMENTS 15428 6/1983 Australia .

OTHER PUBLICATIONS

CA 106(11):83562r, Granular Fertilizer Compositions, Nonaka et al., 1986.
Colby, "Calculating Synergistic . . . Combinations", Weeds 15, (1967), pp. 20–22.

*Primary Examiner*—Ferris Lander
*Attorney, Agent, or Firm*—Sughrue, Mion, Zinn, Macpeak & Seas

[57] ABSTRACT

A granular fertilizer composition superior in plant growth regulating effects is provided which comprises a coating of a mixture of triethylene glycol and a plant growth regulator on a granular fertilizer.

5 Claims, No Drawings

GRANULAR FERTILIZER COMPOSITIONS

Matter enclosed in heavy brackets [ ] appears in the original patent but forms no part of this reissue specification; matter printed in italics indicates the additions made by reissue.

BACKGROUND OF THE INVENTION

The present invention relates to a granular fertilizer composition which comprises a coating of a mixture of triethylene glycol and a plant growth regulator on a granular fertilizer and to a process for preparing it.

In order to exhibit efficiently effects of plant growth regulators, it has been known to use the regulators as mixtures with fertilizers. For preparation of the mixtures, there have been known a method of incorporating the regulators into granular fertilizer and another method of coating the granular fertilizer with the regulators.

However, according to the method of incorporation, for example, in the case of complex fertilizer, since plant growth regulator is incorporated into the fertilizer during the preparation of the fertilizer, the plant growth regulator is susceptible to decomposition due to its contact with acids or/and alkalis which are raw materials for the fertilizer. Furthermore, when off-specification products which have been sifted out are to be reused, the plant growth regulator must be removed therefrom and this requires much troubles. Thus, this method is not practical.

On the other hand, the coating method also has problems caused by organic solvents used in preparation.

SUMMARY OF THE INVENTION

As a result of the inventors' intensive researches in an attempt to solve these problems, it has been found that desired plant growth regulator-containing granular fertilizer compositions free from the above problems can be obtained by coating a mixture of triethylene glycol and a plant growth regulator on granular fertilizers.

DESCRIPTION OF THE INVENTION

The granular fertilizers used in this invention include nitrogeneous fertilizers such as urea, ammonium sulfate, ammonium nitrate. ammonium chloride, urea-form, etc., phosphatic fertilizers such as ammonium phosphate, superphosphate, triple superphosphate, etc. and potassic fertilizers such as potassium chloride, potassium sulfate, etc., two component fertilizers such as nitrogeneous-phosphatic, nitrogeneous-potassic and phosphatic-potassic, three-component fertilizers such as nitrogeneous-phosphatic-potassic and these granular fertilizers which additionally contain elements necessary for growth of plants such as magnesium, boron, manganese, etc. and besides, above-mentioned fertilizers which additionally contain materials for adjustment of components such as gypsum, etc., water insoluble clay minerals such as diatomite, talc, bentonite, etc. used for preventing flotation of fertilizers in application to paddy field and which are granulated by conventional methods.

As the plant growth regulators used in this invention, mention may be made of, for example, (E)-1-(4-chlorophenyl)-4,4-dimethyl-2-(1,2,4-triazol-1-penten-3-ol (referred to as "compound A" hereinafter) or a salt thereof, (E)-1-cyclohexyl-4,4-dimethyl-2-(1,2,4-triazol-1-yl)-1-yl)-1-penten-3-ol (referred to as "compound B" hereinafter) or a salt thereof, 1-(4-chlorophenyl)-4,4-dimethyl-2-(1,2,4-triazol-1-yl) [penten] *pentan*-3-ol (referred to as "compound C" hereinafter) or a salt thereof, etc. These compounds A, B and C are known compounds disclosed in Japanese Patent Publication (Laid-Open) Nos. 25105/81, 111477/80 and 28170/78, respectively.

Content of the plant growth regulator in granular fertilizer composition is usually 0.001–0.02% by weight of the fertilizer and that of fertilizer as active ingredient is usually 8–80% by weight. Application amount of active ingredient (plant growth regulator and fertilizer) is usually 500–1000 g/a.

Triethylene glycol used may be one which is sold for industrial purpose. When addition amount of triethylene glycol is too small, uniform coating on the surface of fertilizer cannot be performed and when too large, this is not only economically disadvantageous, but also causes deterioration of fertilizer components. Thus, it is usually 0.01–5% by weight, preferably 0.3–2% by weight of the granular fertilizer.

Preparation of the granular composition of this invention may be effected typically by dissolving the plant growth regulator in triethylene glycol and, for example, spraying the solution onto granular fertilizer to coat the fertilizer with the solution. Most commonly, there may be employed such method which comprises spraying triethylene glycol containing the plant growth regulator onto granular fertilizer which is being tumbled using apparatuses such as a rotating cylinder, a rotating pan, etc., followed by addition of solidification inhibitors such as talc, diatomite, etc. with continuation of the tumbling.

The following nonlimiting examples and test examples illustrate the invention; all part and % are given by weight, unless otherwise notified.

EXAMPLE 1

A solution of compound A in a solvent was sprayed at the ratio as shown in Table 1 onto 1 Kg of ammonium sulfate-ammonium phosphate fertilizer (N: 13%, $P_2O_5$: 13% and $K_2O$: 13% and blending ratio; ammonium secondary phosphate: 29.3%, ammonium sulfate: 39.6%, potassium chloride: 22.0% and gypsum: 9.1%) of 1–4 mm in particle diameter which was under rolling action at 80° C. on a pan type granulator and then, 0.5% of talc was added to the fertilizer under tumbling to obtain ammonium sulfate-ammonium phosphate fertilizer compositions. States of the compositions as prepared are shown in Table 1.

TABLE 1

| Solvent | | Compound A | | |
|---|---|---|---|---|
| Kind | Addition amount (% based on fertilizer) | Addition amount (% based on fertilizer) | Solubility | Odor of product |
| Triethylene glycol | 0.3 | 0.007 | Soluble | Odorless |
| | 0.5 | 0.007 | " | " |
| Ethylene glycol (Comparative) | 0.3 | 0.007 | Insoluble | Odorless |
| | 0.5 | 0.007 | " | " |
| n-Nonyl alcohol (Comparative) | 0.3 | 0.007 | Soluble | Unpleasant odor |
| | 0.5 | 0.007 | " | Unpleasant odor |
| Machine | 0.3 | 0.007 | Insoluble | Oil odor |

TABLE 1-continued

| Solvent | | Compound A | | |
|---|---|---|---|---|
| Kind | Addition amount (% based on fertilizer) | Addition amount (% based on fertilizer) | Solubility | Odor of product |
| oil (Comparative) | 0.5 | 0.007 | " | " |

Note
"Solubility" is of compound A in solvent

A solution prepared by dissolving 0.04% (based on the weight of fertilizer) of compound A in 0.3% (based on the weight of fertilizer) of triethylene glycol was sprayed onto 1 Kg of ammonium nitrate-ammonium phosphate fertilizer (N: 5%, $P_2O_5$: 4% and $K_2O$: 5% and blending ratio; ammonium primary phosphate: 9.0%, ammonium nitrate: 7.0%, ammonium sulfate: 15.2%, potassium sulfate: 10.9% and gypsum: 57.5%) of 1-4 mm in particle diameter which was under tumbling at 70° C. on a pan type granulator and then, 0.5% of talc was added thereto still under tumbling to obtain an ammonium nitrate-ammonium phosphate fertilizer composition.

EXAMPLE 3

A solution prepared by dissolving 0.01% (based on the weight of fertilizer) of compound A in 1% (based on the weight of fertilizer) of triethylene glycol was sprayed onto 1 Kg of urea fertilizer (N: 18%, $P_2O_5$: 18% and $K_2O$: 18% and blending ratio: ammonium secondary phosphate: 40.2%, urea: 24.5%, potassium chloride: 30.1% and gypsum: 5.2%) of 1-4 mm in particle diameter which was under tumbling at 60° C. on a pan type granulator and then, 0.5% of talc was added thereto still under tumbling to obtain an urea fertilizer composition.

TEST EXAMPLE 1

Rice (Oryza sativa L. cv: Koshihikari) was cultivated in a paddy field and the granular fertilizer composition of this invention according to Example 1(triethylene glycol: 0.5% and compound A: 0.007%), a wettable powder containing compound A as an active ingredient and a control granular fertilizer were respectively applied to the surface of the paddy field on the 18th day before heading. Thereafter, cultivation was continued, and culm length and panicle length of the rice plants, degree of lodging of the plants and yield of rice were measured.

The tests were repeated three times for one test plot of 10 $m^2$ and the results are shown in average values in Table 2.

In the case of the control granular fertilizer, culm length was long end degree of lodging was high, therefore the yield was small. When compound A was used along, culm length was shortened and lodging of the plants did not occur, but panicle growth was also inhibited, and hence the yield increasing effect was small.

On the other hand, in the test plot of the granular fertilizer composition of this invention, culm growth was inhibited and thus lodging of the plants was prevented and furthermore, the inhibitory effect on the panicle growth was a little, resulting in increase of yield.

TABLE 2

| Test plot | Application amount (g/a) | Culm length (cm) | Panicle length (cm) | Degree of lodging[a] | Weight of hulled rice (Kg/a) |
|---|---|---|---|---|---|
| Granular fertilizer of this invention | 3000 | 78.6 | 19.0 | 0.3 | 50.6 |
| Compound A | 0.21 (a.i.) | 74.3 | 17.9 | 0 | 48.5 |
| Control granular fertilizer (N 13%, $P_2O_5$ 13%, $K_2O$ 13%) | 3000 | 90.3 | 19.8 | 3.3 | 42.1 |
| Non-treatment | — | 87.4 | 18.8 | 2.3 | 43.3 |

[a]0: no lodging
up to 5: complete lodging

What is claimed is:

1. A granular fertilizer composition which comprises a granular fertilizer coated with a mixture of triethylene glycol and a plant growth regulator selected from the group consisting of (E)-1-(4-chlorophenyl)-4,4-dimethyl-2-(1,2,4-triazol-1-yl)-1-penten-3-ol or a salt thereof, (E)-1-cyclohexyl-4,4-dimethyl-2-(1,2,4-triazol-1-yl)-1-penten-3-ol or a salt thereof or 1-(4-chlorophenyl)-4,4-dimethyl-2-(1,2,4-triazol-1-yl-[penten]*pentan*-3-ol or a salt thereof, wherein the amount of plant growth regulator is 0.001% *to 0.2%* by weight of the fertilizer and that of triethylene glycol is 0.1-5% by weight of the fertilizer.

2. A granular fertilizer composition according to claim 1 wherein amount of the granular fertilizer is 8-80% by weight of the composition.

3. A process for preparing a granular fertilizer composition which comprises coating a granular fertilizer with a mixture of triethylene glycol and a plant growth regulator selected from the group consisting of (E)-1-(4-chlorophenyl)-4,4-dimethyl-2-(1,2,4-triazol-1-yl)-1-penten-3-ol or a salt thereof, (E)-1-cyclohexyl-4,4-dimethyl-2-(1,2,4-triazol-1-triazol-1-yl)-1-penten-3-ol or a salt thereof or 1-(4-chlorophenyl)-4,4-dimethyl-2-(1,2,4-triazol-1-yl-[penten]*pentan*-3-ol or a salt thereof, wherein the amount of plant growth regulator is 0.001% *to 0.2%* by weight of the fertilizer and that of triethylene glycol is 0.1-5% by weight of the fertilizer.

4. A process according to claim 3 wherein amount of the granular fertilizer is 8-80% by weight of the composition.

5. A process according to claim 3 which comprises coating a granular fertilizer with a solution of a plant growth regulator in triethylene glycol.

* * * * *